US012631705B2

(12) United States Patent
Maciejewski et al.

(10) Patent No.:  US 12,631,705 B2
(45) Date of Patent:      May 19, 2026

(54) NOISE-REDUCED MAGNETIC RESONANCE TOMOGRAPHY UNIT

(71) Applicant: Siemens Healthineers AG, Forchheim (DE)

(72) Inventors: Bernd Maciejewski, Markt Bibart (DE); Martin Schröder, Möhrendorf (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/609,486

(22) Filed: Mar. 19, 2024

(65) Prior Publication Data

US 2024/0319302 A1      Sep. 26, 2024

(30) Foreign Application Priority Data

Mar. 20, 2023      (DE) ...................... 10 2023 202 429.2

(51) Int. Cl.
*A61B 5/05* (2021.01)
*A61B 5/055* (2006.01)
*G01R 33/385* (2006.01)

(52) U.S. Cl.
CPC .......... *G01R 33/3854* (2013.01); *A61B 5/055* (2013.01); *G01R 33/3858* (2013.01)

(58) Field of Classification Search
CPC .............. A61B 5/055; G01R 33/34007; G01R 33/3854; G01R 33/3858
See application file for complete search history.

(56) References Cited

U.S. PATENT DOCUMENTS

| | | | | |
|---|---|---|---|---|
| 6,437,568 | B1 * | 8/2002 | Edelstein ........... | G01R 33/3854 |
| | | | | 324/309 |
| 6,954,068 | B1 * | 10/2005 | Takamori ........... | G01R 33/3854 |
| | | | | 324/318 |
| 2012/0229138 | A1 | 9/2012 | Saha | |
| 2015/0002154 | A1 * | 1/2015 | Lazar ............... | G01R 33/34046 |
| | | | | 324/322 |
| 2020/0146639 | A1 * | 5/2020 | Campagna ........... | A61B 6/4085 |
| 2022/0378385 | A1 * | 12/2022 | Campagna ........... | A61B 6/0407 |

FOREIGN PATENT DOCUMENTS

| | | |
|---|---|---|
| DE | 102012101879 A1 | 9/2012 |
| WO | 2009031092 A1 | 3/2009 |

* cited by examiner

*Primary Examiner* — Christopher L Cook
(74) *Attorney, Agent, or Firm* — Lempia Summerfield Katz LLC

(57) ABSTRACT

A magnetic resonance tomography unit includes a patient tunnel and a gradient coil. A first holding structure holds the patient tunnel in an application-appropriate relative position to the magnetic resonance tomography unit, while a second holding structure holds the gradient coil. The first holding structure and the second holding structure have no vibration-transmitting mechanical coupling.

6 Claims, 2 Drawing Sheets

NOISE-REDUCED MAGNETIC RESONANCE TOMOGRAPHY UNIT

CROSS REFERENCE TO RELATED APPLICATIONS

This application claims the benefit of DE 10 2023 202 429.2 filed on Mar. 20, 2023, which is hereby incorporated by reference in its entirety FIELD Embodiments relate to a magnetic resonance tomography unit that emits less sound and minimizes vibrations or sound transmission.

BACKGROUND

Magnetic resonance tomography units are imaging apparatuses that so as to image the examination object align nuclear spins of the examination object with a strong external magnetic field and excite the nuclear spins by an alternating magnetic field so as to facilitate precession about this alignment. The precession or return of the spins from this excited state to a lower energy state in turn generates in response an alternating magnetic field that is received via antennas.

With the aid of magnetic gradient fields, a spatial coding is impressed on the signals, that subsequently enables the received signal to be assigned to a volume element. The received signal is then evaluated and a three-dimensional imaging representation of the examination object is provided. It is preferred that in order to receive signals, local receiving antennae, e.g., local coils, are used, that are arranged directly at the examination object so as to achieve an improved signal-noise ratio.

In order to generate gradient fields, resistive coils also referred to as gradient coils are subjected to currents of several hundred amperes and are switched on and off in periods of milliseconds. Extreme forces act on the windings, leading to deformation even in the case of a rigid construction. At these switching speeds, the deformations in turn generate structure-borne noise in the acoustic range, that is also emitted into the environment.

As the strength of the gradient fields to be achieved increases, the acoustic stress on the patient and vibrations become intolerable.

BRIEF SUMMARY AND DESCRIPTION

The scope of the present disclosure is defined solely by the claims and is not affected to any degree by the statements within this summary. The present embodiments may obviate one or more of the drawbacks or limitations in the related art. Independent of the grammatical term usage, individuals with male, female or other gender identities are included within the term.

Embodiments provide a magnetic resonance tomography unit that emits less sound and minimizes vibrations or sound transmission, respectively, to the patient.

The magnetic resonance tomography unit includes a patient tunnel. The patient tunnel refers to the cylindrical hollow structure that extends through an opening of a field magnet. Cylindrical is understood in this case in the geometric meaning and includes a patient tunnel that has a circular, elliptical, polygonal, or mixed cross-sectional shape. The patient tunnel accommodates the patient for image acquisition using the magnetic resonance tomography unit, for example on a patient couch. A wall of the hollow structure is arranged between the patient and the magnetic resonance tomography unit, for example between the patient and the gradient coil and the field magnet, so that the patient is shielded from the gradient coil at least to a limited extent in terms of acoustics/vibration. The wall may include of multiple layers, for example at least one rigid layer or structure that may absorb the weight forces of the patient and the patient couch. Another conceivable feature is a layer for sound insulation, that is configured so as to attenuate sound emissions from the gradient coil in the direction of the patient.

Furthermore, the magnetic resonance tomography unit includes a gradient coil for generating magnetic gradient fields for spatial coding during image acquisition. The gradient coil includes a support structure, for example a rigid cylinder or a tube, on or in which the conductors of the gradient coil are arranged and mechanically fixed for magnetic field generation. The support structure is configured for example so as to absorb the forces that act on the conductors of the gradient coil during operation due to the magnetic fields largely without deforming the conductors, in order to reduce or avoid changes in the geometry of the gradient coil that are caused thereby and influence the generated magnetic field in an unforeseen manner. In addition, such deformations are the cause of unwanted noise emissions from the gradient coil.

The patient tunnel, also referred to as the support tube, includes a first holding structure in order to arrange or fix it in a predetermined relative position to the magnetic resonance tomography unit. The patient tunnel extends in the predetermined position through the field magnet so that a patient located in the patient tunnel may be positioned at least partially in the preferred area for magnetic resonance imaging, the field of view (FoV) or isocenter. The FoV is characterized by a homogeneous static magnetic field $B0$. The first holding structure may include various, for example non-ferromagnetic elements such as supports, bent sheet metal parts or milled parts.

It is also possible to have an elastic, vibration-damping first holding structure, for example made of plastic or foam, that supports or positions the patient tunnel.

The patient tunnel may also include two first holding structures, that are for example arranged at two opposite ends along the longitudinal direction of the patient tunnel. A first holding structure may also be included that is arranged additionally or alternatively, for example, centrally, along the longitudinal extent of the patient tunnel.

The gradient coil includes a second holding structure that is configured so as to arrange the gradient coil in an application-appropriate relative position to the magnetic resonance tomography unit. In the predetermined position, the gradient coil extends through the field magnet in such a manner that the conductors of the gradient coil may generate field gradients in the isocenter or FoV when suitable currents are applied. For example, the gradient coil surrounds the patient tunnel on the outside at least in the area of the FoV. The gradient coil and the patient tunnel may, for example, be arranged concentrically to each other.

The above description of the first holding structure applies analogously to the second holding structure.

For example, the first holding structures and/or second holding structures are arranged outside the field magnet. The field magnet is considered to be not only the field-generating winding, but also the surrounding housing, and in the case of superconducting field magnets for example also the surrounding cryostat. As already described, the field magnet includes a feedthrough in which the homogeneous static $B0$ magnetic field is provided with the FoV and in which the patient tunnel and the gradient coils are arranged. Outside the field magnet is also considered to be outside this feedthrough. For example, outside means at a distance from the field magnet in a longitudinal direction of the feedthrough, in other words at a distance from the field magnet in front of and/or behind the feedthrough.

In this case, the first holding structure and the second holding structure have no vibration-transmitting mechanical coupling to each other. In other words, the first holding structure and the second holding structure are decoupled with regard to the transmission of mechanical vibrations.

Mechanical coupling is generally defined here as a force-transmitting connection. The patient tunnel and the gradient coil are held in a predetermined relative position in the magnetic resonance tomography unit so that they do not change under the influence of external forces, for example weight forces from a patient or by moving a patient table. This is a mechanical coupling, but it is configured not to transmit any mechanical, for example acoustic, vibrations from the gradient coil to the patient tunnel or at least to dampen them considerably, for example by more than 40 dB, 60 dB or 80 dB. For example, the gradient coil and the patient tunnel also have no direct mechanical coupling in that they are in direct contact with each other or are directly connected to each other by a single structural element.

Different embodiments are described below.

In an advantageous manner, the decoupling of the patient tunnel from the gradient coil reduces vibrations, for example in the audible acoustic frequency range, significantly reducing the noise level in the patient tunnel.

In an embodiment of the magnetic resonance tomography unit, the patient tunnel and the first support structure have no vibration-transmitting mechanical coupling to the rest of the magnetic resonance tomography unit. In other words, there is no mechanical element that directly mechanically connects the patient tunnel to the magnetic resonance tomography unit and that transmits vibrations, for example in an acoustic frequency range, from the magnetic resonance tomography unit to the patient tunnel.

For example, this is achieved by connecting the patient tunnel directly to a mounting platform via the first holding structure. For example, direct is considered here to mean that the first holding structure is not connected to the rest of the magnetic resonance tomography unit, that is then in turn connected to the mounting platform.

A mounting platform is a mechanical reference mass on which the magnetic resonance tomography unit is set up for operation, for example a concrete floor or foundation in a building. However, an acoustic mounting platform of sufficient mass that is decoupled from the building may be used. In this case, the patient tunnel is connected directly to the mounting platform via the first holding structure or first holding structures, without direct contact or connection to the magnetic resonance tomography unit. Only electrical connections to the magnetic resonance tomography unit are conceivable, but these are for example implemented using flexible cables in order to minimize vibration transmission. In this manner, the relative position of the patient tunnel in relation to the magnetic resonance tomography unit is defined and fixed even without direct sound-transmitting contact. The mounting platform has such a large mass and/or rigidity that the forces exerted by the magnetic resonance tomography unit or the gradient coil via the second holding structure do not cause any vibrations or only cause insignificant vibrations via the mounting platform in the patient tunnel positioned thereon using the first holding structure, and for example do not cause any acoustic noise.

In this manner, the separate attachment to the mounting platform advantageously prevents a vibration-transmitting mechanical coupling from the gradient coil or the magnetic resonance tomography unit to the patient tunnel from contributing to the propagation of sound.

Only the patient tunnel may be directly connected to the mounting platform via the first holding structure, without direct vibration-transmitting mechanical elements to the magnetic resonance tomography unit. However, a combination with the embodiment described below is also possible.

In an embodiment of the magnetic resonance tomography unit, the gradient coil and the second holding structure have no vibration-transmitting mechanical coupling to the magnetic resonance tomography unit and the patient tunnel.

The gradient coil is connected directly to the mounting platform via the second holding structure or second holding structures, without direct contact or connection to the magnetic resonance tomography unit. Only electrical connections to the magnetic resonance tomography unit are conceivable, but these are for example implemented with flexible cables in order to minimize vibration transmission. The relative position of the gradient coil in relation to the magnetic resonance tomography unit is defined and fixed even without direct sound-transmitting contact.

In an embodiment, both the gradient coil and the patient tunnel are decoupled from the magnetic resonance tomography unit via the mounting platform in order to limit the transmission of vibrations at the source and to improve shielding through the patient tunnel.

Vibration decoupling of the gradient coil as a noise source leads to a further reduction in the patient's noise level.

In an embodiment of the magnetic resonance tomography unit, the first holding structure and/or the second holding structure includes a vibration decoupling element. A vibration decoupling element is a mechanical connecting element that transmits force between two points but reduces the transmitted amplitude, for example by more than 30 dB, 60 dB or 80 dB, at least for vibrations of a predetermined frequency or frequency range. Examples of this are hydraulic shock absorbers in conjunction with spring elements. Elastomers such as a Sylomer may be used. Such vibration decoupling elements may, for example, be arranged as buffers or pads at one end of the holding structure, for example between the holding structure and the patient tunnel or the gradient coil at the proximal end and/or at the distal end, for example between the mounting platform and the support structure.

A vibration decoupling element in a holding structure may reduce sound propagation via the first holding structure and/or the second holding structure and reduce the noise level.

In an embodiment of the magnetic resonance tomography unit, the first and/or second holding structure includes a position adjustment apparatus. The term position adjustment apparatus is used here to refer to an apparatus that allows the position of the patient tunnel or the gradient coil to be changed to a predetermined extent without irreversibly deforming the holding structure, even after the holding structure has been attached to the distal end, for example the mounting platform or the floor. If, for example, the gradient coil and/or the patient tunnel are connected to the mounting platform via the holding structure and not directly to the rest of the magnetic resonance tomography unit, their relative position to the magnetic resonance tomography unit cannot be fixed from the moment of manufacture. Due to tolerances, for example when drilling the mounting holes in a foundation, it may be necessary to adjust the relative position in relation to the rest of the magnetic resonance tomography unit. The position adjustment apparatus may, for example, be provided by two sub-elements of the holding structure, that are screwed together in a displaceable manner via slotted holes. Distances may be used that may be adjusted via threads and have two sub-elements that move in one direction, that enables a finer adjustment. Adjustment is possible horizontally or also vertically as height adjustment, using three position adjustment apparatuses also in all three spatial axes simultaneously.

the position adjustment apparatus also allows fine adjustment of the relative position when mounted separately on a foundation.

In an embodiment of the magnetic resonance tomography unit, the patient tunnel includes a body coil. For example, the body coil may be molded into a tubular structure of the patient tunnel or arranged on its side facing away from the patient.

A combination of patient tunnel and body coil enables a more compact design in the radial direction. The space thus gained may be used, for example, for additional sound insulation.

DETAILED DESCRIPTION

Figure 1:
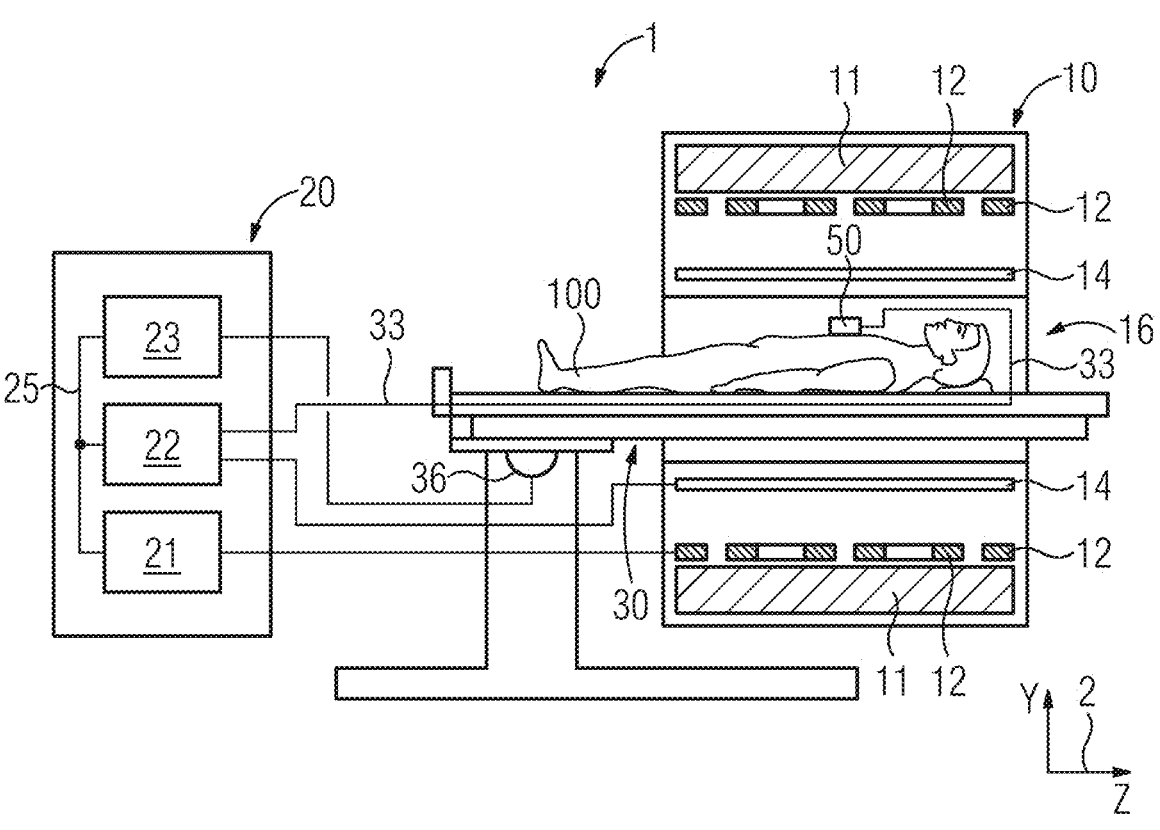
FIG. 1 depicts a schematic illustration of a magnetic resonance tomography unit according to an embodiment.

FIG. 1 depicts a schematic overview of an embodiment of a magnetic resonance tomography unit 1.

The magnetic resonance tomography unit 1 includes a magnet unit 10 with a field magnet 11 that generates a static magnetic field B0 for the alignment of nuclear spins of samples or the patient 100 in a recording area, that is also referred to as the field of view (FoV). The recording area is characterized by an extremely homogeneous static magnetic field B0, wherein the homogeneity relates for example to the magnetic field strength or magnitude. The recording area is almost spherical and arranged in a patient tunnel 16 that extends in a lengthwise direction 2 through the magnet unit 10. A patient couch 30 may be moved in the patient tunnel 16 by the drive unit 36. The field magnet 11 is usually a superconducting magnet that may provide magnetic fields with a magnetic flux density of up to 3T, in the case of latest models even higher. However, it is also possible for lower magnetic field strengths to also use permanent magnets or electromagnets with normal conducting coils.

Furthermore, the magnet unit 10 includes gradient coils 12 that are configured so as to superimpose temporally and spatially variable magnetic fields in three spatial directions on the magnetic field B0 for spatial differentiation of the detected imaging areas in the examination volume. The gradient coils 12 may be coils of normal conducting wires that may create mutually orthogonal fields in the examination volume.

The magnet unit 10 also includes a body coil 14 that is configured so as to radiate a radio frequency signal, that is supplied via a signal line, into the examination volume and to receive resonance signals that are emitted by the patient 100 and deliver them via a signal line.

A control unit 20 supplies the magnet unit 10 with the different signals for the gradient coils 12 and the body coil 14 and evaluates the received signals.

The control unit 20 includes a gradient controller 21 that is configured so as to supply the gradient coils 12 via supply lines with variable currents that provide in a temporally coordinated manner the desired gradient fields in the examination volume.

Furthermore, the control unit 20 includes a radio frequency unit 22 that is configured so as to generate a radio frequency pulse that has a predetermined time course, amplitude, and spectral power distribution so as to excite a magnetic resonance of the nuclear spins in the patient 100. In so doing, pulse powers in the range of kilowatts may be achieved. The excitation signals may be radiated via the body coil 14 or also via a local transmitting antenna into the patient 100.

A controller 23 communicates with the gradient controller 21 and the radio frequency unit 22 via a signal bus 25.

So as to receive the magnet resonance signal, a local coil 50 is arranged on the patient 100 in the patient tunnel 16 in order to detect magnet resonance signals from an examination region in close proximity with the highest possible signal-to-noise ratio. The local coil 50 is in signal connection with a receiver in the radio frequency unit 22 via a connection line 33.

The local coil 50 may be configured so as to emit a radio frequency pulse to excite the nuclear spins in the patient 100 and thus the body coil 14 may be omitted.

Figure 2:
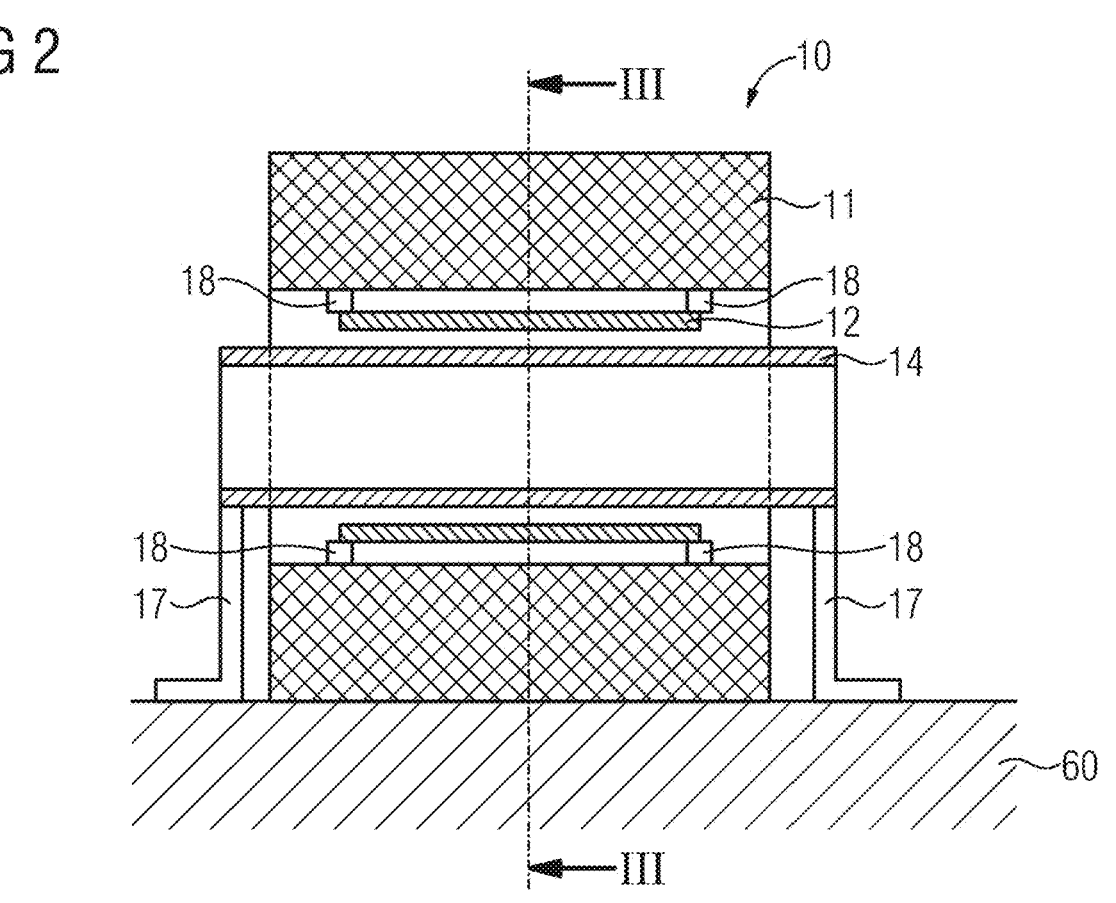
FIG. 2 depicts a schematic representation of a magnet unit of an embodiment of the magnetic resonance tomography unit according to an embodiment.

FIG. 2 depicts a schematic view of an embodiment of the magnetic resonance tomography unit 1. In order to improve the overview, only the essential elements are shown.

FIG. 2 depicts the magnet unit 10 with the components arranged in or on it. The field magnet 11 or its cryostat has a feedthrough in which the static and homogeneous magnetic field B0 that is required for image acquisition using magnetic resonance tomography is provided in the isocenter or FoV. In the feedthrough, the gradient coils 12 are arranged around this isocenter along the inner wall of the cryostat in order to provide the gradient fields in the FoV. The gradient coil 12 may include multiple windings of electrical conductors that are mounted on or molded into a support structure, for example a rigid tube, in order to absorb the forces caused by the magnetic fields. Due to the switching frequencies of the gradient currents in the hertz to kilohertz range, these forces also generate vibrations in the gradient coil 12, that are also emitted as acoustic noise.

The patient tunnel 16, also known as the support tube, is located inside the gradient coil 12, since the patient couch 30 for the patient 100 is arranged in it. The patient tunnel 30 protects the patient 100 from contact with the gradient coil 12 and the body coil 14, that are often arranged on the wall of the patient tunnel 16 that faces away from the patient 100 or in the wall of the support tube.

The relative position of the patient tunnel 14 to the field magnet 11 and thus the patient 100 in it must not change during image acquisition, since otherwise movement artifacts will be caused in the captured images. The same applies to the gradient coil 12.

In previous implementations, the gradient coil 12 and the patient tunnel 30 are therefore connected to the field magnet 11 in a predetermined fixed position, for example by screwing, directly or via supports.

However, especially in systems with particularly powerful gradient coils 12 or gradient control units 21, the vibrations of the gradient coil 12 during operation are so violent that noise with values of 100 dBA and above is emitted. Due to the rigid mechanical coupling in the prior art, vibrations are also transmitted from the gradient coil 12 to the field magnet 11 and the patient tunnel 30 and are also radiated from these to the patient 100.

Embodiments decouple the components, for example the patient tunnel 30 with the patient 100, from the noise source, the gradient coil 12, acoustically or with respect to vibration.

In the embodiment of FIG. 2, this is achieved by arranging the patient tunnel 30 on first holding structures 17 and fixing it to them. In the embodiment of FIG. 2, however, the first holding structures are not directly connected to the rest of the magnetic resonance tomography unit 1, for example the magnet unit 10, at the distal end or the end that is spaced apart from the patient tunnel 16, as is common in the prior art, and are thus coupled for acoustic vibrations. In lieu of this, the ends of the first holding structures 17 that are spaced apart from the patient tunnel 16 are configured so as to be connected directly to a mounting platform 60. In the embodiment shown in FIG. 2, the patient tunnel 16 protrudes from the feedthrough of the field magnet 11. The first holding structures 17 are arranged at the opposite ends of the patient tunnel 16 at such a distance from the magnet unit 10 that they connect the patient tunnel 16 to the mounting platform 60 without mechanical contact or connection with the rest of the magnetic resonance tomography unit 1 or the magnet unit 10.

The term mounting platform 60 refers to a reference mass that is large enough to absorb the forces exerted by the patient tunnel via the first holding structures 17 without any significant change in position. The mounting platform 60 is decoupled from the magnetic resonance tomography unit 1 or the gradient coil 12 with respect to vibrations, for example by damping elements or by such a large mass and/or rigidity that the vibrations in the Hertz to kilohertz range that occur during image acquisition are damped by more than 30 dB, 60 dB, 90 dB or 120 dB up to the first holding structure 17. The mounting platform 60 may be a solid concrete floor, for example. One or more solid plates or platforms are also conceivable as the mounting platform 60, that are mounted in a vibration-damping manner with respect to the surroundings and/or with respect to each other.

In FIG. 2, the gradient coil 12 is fixed to the field magnet 11 using second holding structures 18. The second holding structures 18 may, for example, be rigid supports that are screwed to the housing of the field magnet 11 and the gradient coil 12 or attached to it in some other manner. Vibration decoupling then takes place solely via the mounting platform 60.

For example, the second holding structure 18 itself has vibration-damping properties or a separate vibration damper, so that the amplitude of vibrations is reduced by more than 30 dB, 60 dB or 90 dB when passing through the second holding structure 18. For example, the second holding structure 18 may consist entirely or partially of an elastomer such as Sylomer, in which the gradient coil 12 is embedded or mounted on. Shock absorbers are also conceivable as vibration dampers that are optimized for the frequency range of the gradients.

The first holding structure 17 may include such vibration-damping elements.

In an embodiment, it is also conceivable that the second holding structures 18, as already described for the first holding structures 17 in connection with the patient tunnel 16, the gradient coil 12 is connected directly to the mounting platform 60 without vibration coupling to the rest of the magnetic resonance tomography unit 1 and for example to the patient tunnel 16. For example, the gradient coil 12 or a mechanical extension of the gradient coil 12 may protrude from the feedthrough of the field magnet 11 and second holding structures 18 may fix the gradient coil 12 to the mounting platform 60 at opposite ends. In this case, it is advantageously prevented that the vibrations cause other parts of the magnetic resonance tomography unit 1 to vibrate and thus emit noise.

If the gradient coil 12 is decoupled in this manner from the magnetic resonance tomography unit 1 for vibrations in the acoustic frequency range, it may be possible to dispense with decoupling the patient tunnel 16 from the rest of the magnetic resonance tomography unit or to do so more simply.

Conversely, the noise emission may be further improved by mounting the patient tunnel 16 and gradient coil 12 separately directly on the mounting platform 60.

Figure 3:
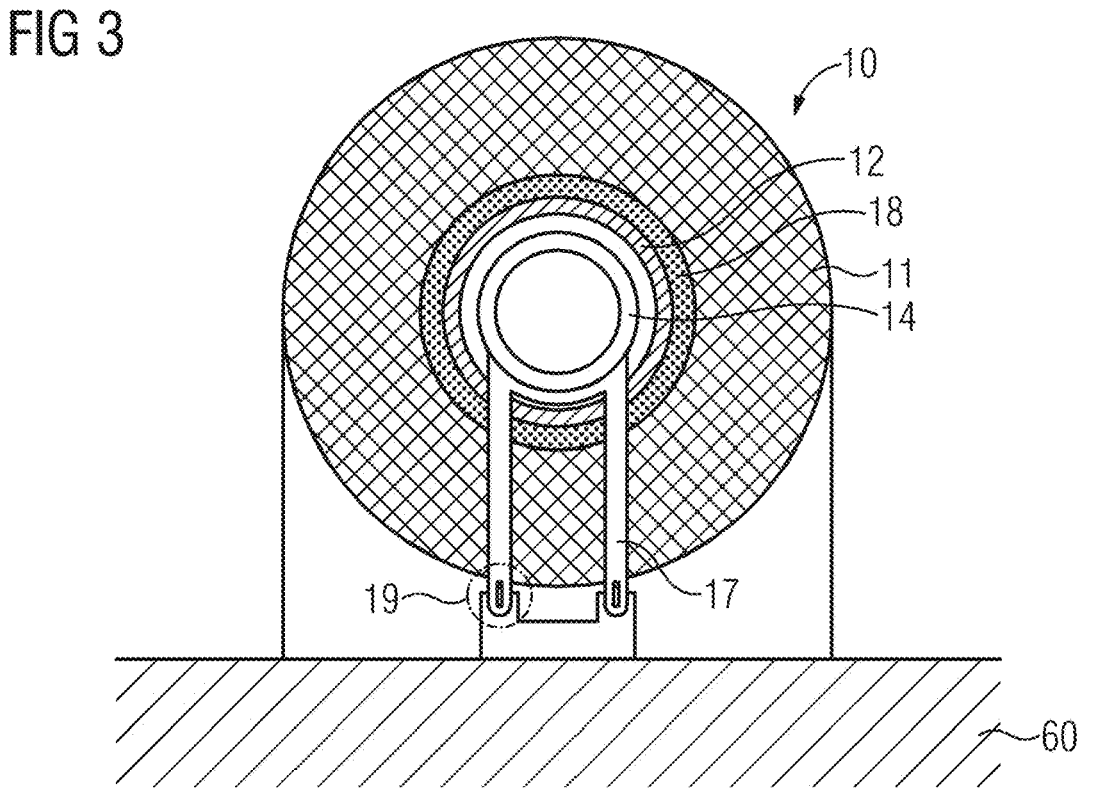
FIG. 3 depicts a schematic view of a magnetic unit of an embodiment of the magnetic resonance tomography unit.

FIG. 3 depicts the embodiment of the magnetic resonance tomography unit 1 or the magnet unit 10 of FIG. 2 in a partial cross-section along the axis A-A. The first holding structure 17 and the patient tunnel 16 are added in a top view. Identical reference characters correspond to identical objects.

In FIG. 3, a position adjustment apparatus 19 is schematically indicated in the first holding structure 12 for example. In the embodiment shown, the first holding structure 17 is not attached to the magnetic resonance tomography unit 1 or its magnet unit 10, but only to the mounting platform 60 during assembly on site. This means that the relative position of the patient tunnel 16 to the magnet unit 10 cannot be established exactly during manufacture. For example, the mounting platform 60 may have tolerances, for example on a concrete floor, and holes in the concrete may also cause deviations. For this reason, the first holding structure 17 and/or the second holding structure 18 for example has a position adjustment apparatus 19.

The position adjustment apparatus 19 may, for example, include the first holding structure 17 or the second holding structure 18 being made in two parts. One of the parts has an elongated hole in which one or more screws are arranged, that connect the two parts to one another in a displaceable manner. Other position adjustment apparatuses 19 that allow adjustment in one axis are also conceivable, such as a length adjustment using screws that have two opposite-running threads. In addition to the vertical adjustment, the position adjustment apparatus 19 may also have corresponding adjustment facilities in 1 or 2 axes in the horizontal plane. Other position adjustment apparatuses 19 that have two or three axes may be used, wherein the axes are not necessarily orthogonal to each other, but merely span a two- or three-dimensional space.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance tomography unit comprising:

a patient tunnel comprising a first holding structure configured so as to arrange the patient tunnel in a first application-appropriate relative position to the magnetic resonance tomography unit, wherein the first holding structure is attached directly to a mounting platform and is not mechanically connected to the magnetic resonance tomography unit such that the patient tunnel has no vibration-transmitting mechanical coupling to the magnetic resonance tomography unit; and a gradient coil comprising a second holding structure configured so as to arrange the gradient coil in a second application-appropriate relative position to the magnetic resonance tomography unit;

wherein the first holding structure and the second holding structure have no vibration-transmitting mechanical coupling to each other;

wherein the first holding structure and/or the second holding structure includes a position adjustment apparatus comprising at least one or more screws that provide a length adjustment for a position of the first holding structure and/or second holding structure, wherein a change in a position of the patient tunnel or the gradient coil is performed without irreversibly deforming a respective holding structure.

2. The magnetic resonance tomography unit of claim 1, wherein the first holding structure is configured so as to connect the patient tunnel directly to a mounting platform.

3. The magnetic resonance tomography unit of claim 1, wherein the gradient coil and the second holding structure have no vibration transmitting mechanical coupling to the magnetic resonance tomography unit.

4. The magnetic resonance tomography unit of claim 3, wherein the second holding structure is configured so as to connect the gradient coil to a mounting platform.

5. The magnetic resonance tomography unit of claim 1, wherein the first holding structure and/or the second holding structure includes a vibration decoupling element.

6. The magnetic resonance tomography unit of claim 1, wherein the patient tunnel includes a body coil.

* * * * *